United States Patent
Gannaway et al.

(10) Patent No.: US 10,551,519 B2
(45) Date of Patent: Feb. 4, 2020

(54) TECHNIQUES FOR CO-SITING A METAL DETECTOR WITH ANOTHER DETECTOR

(71) Applicant: Roke Manor Research Limited, Romsey, Hampshire (GB)

(72) Inventors: Julian Nolan Gannaway, Romsey (GB); Richard Alexander Meyers, Romsey (GB)

(73) Assignee: Roke Manor Research Limited, Romsey, Hampshire (GB)

( * ) Notice: Subject to any disclaimer, the term of this patent is extended or adjusted under 35 U.S.C. 154(b) by 484 days.

(21) Appl. No.: 14/572,001

(22) Filed: Dec. 16, 2014

(65) Prior Publication Data

US 2015/0168458 A1  Jun. 18, 2015

(30) Foreign Application Priority Data

Dec. 18, 2013 (GB) .................................. 1322423.3

(51) Int. Cl.
*G01R 1/30* (2006.01)
*G01N 27/72* (2006.01)
(Continued)

(52) U.S. Cl.
CPC ........... *G01V 3/107* (2013.01); *G01N 24/084* (2013.01); *G01R 33/4808* (2013.01)

(58) Field of Classification Search
CPC ........ G01V 3/107; G01V 3/101; G01V 3/104; G01V 3/10; G01V 3/105; G01V 3/102;
(Continued)

(56) References Cited

U.S. PATENT DOCUMENTS 3,742,341 A * 6/1973 Clowes .................. G01V 3/101
324/329
4,293,816 A * 10/1981 Johnson ................. G01V 3/107
324/329
(Continued)

FOREIGN PATENT DOCUMENTS

EP   1923724 A2   5/2008
GB   2123559 A    2/1984
(Continued)

OTHER PUBLICATIONS

Apr. 21, 2014—(GB) Search Report—App GB1322423.3.
(Continued)

*Primary Examiner* — Lee E Rodak
(74) *Attorney, Agent, or Firm* — Banner & Witcoff, Ltd.

(57) ABSTRACT

In a first technique one or more tuned circuits ("traps") are placed in series in the metal detector coil, tuned to the operating frequency of the other sensor. In another technique a single turn coil of wire, or a small number of turns coil, is used as the metal detector coil, in combination with a step up transformer at the coil feed, to increase the EMF of the coil. In a further technique, the metal detector coil is formed in a plane that has regard to the sensing field of the other sensor. In another technique, the feed for the metal detector coil comprises a twisted pair of wires, which are routed along an axis in order to try to minimize and equalize the effect of the metal detector feed on the operation of the other antenna.

10 Claims, 6 Drawing Sheets

Trap in Multi-turn Coil (51) Int. Cl.
*G01V 3/10* (2006.01)
*G01R 33/48* (2006.01)
*G01N 24/08* (2006.01)

(58) Field of Classification Search
CPC ........ G01V 3/15; G01V 3/108; G01D 5/2006; G01N 24/084; G01R 33/4808
See application file for complete search history.

(56) References Cited

U.S. PATENT DOCUMENTS

| | | | | |
|---|---|---|---|---|
| 5,043,666 A | * | 8/1991 | Tavernetti | G01R 29/085 324/202 |
| H1217 H | * | 8/1993 | Phelps | 324/326 |
| 5,294,886 A | * | 3/1994 | Duerr | G01R 33/3685 324/318 |
| 6,219,570 B1 | * | 4/2001 | Mueller | G01R 33/283 324/318 |
| 6,541,966 B1 | * | 4/2003 | Keene | G01V 3/08 324/225 |
| 2003/0107377 A1 | * | 6/2003 | Uzman | G01V 3/101 324/327 |
| 2004/0046550 A1 | * | 3/2004 | Kondo | G01V 3/104 324/233 |
| 2008/0111545 A1 | * | 5/2008 | Crowley | G01V 3/101 324/234 |
| 2008/0315874 A1 | | 12/2008 | Crowley | |
| 2011/0193558 A1 | | 8/2011 | Crowley et al. | |
| 2011/0215928 A1 | * | 9/2011 | Soto | G01V 3/10 340/572.1 |
| 2012/0130054 A1 | * | 5/2012 | Peterson | C07K 1/22 530/422 |
| 2013/0049745 A1 | * | 2/2013 | Lyon | G01V 3/104 324/239 |
| 2013/0181718 A1 | * | 7/2013 | Richardson | G01V 3/101 324/327 |
| 2015/0084632 A1 | * | 3/2015 | Wilhelm | G01R 33/282 324/318 |
| 2015/0362614 A1 | * | 12/2015 | Obayashi | G01V 3/104 324/207.17 |

FOREIGN PATENT DOCUMENTS

| | | |
|---|---|---|
| JP | 2007170885 A | 7/2007 |
| WO | 2012027783 A1 | 3/2012 |

OTHER PUBLICATIONS

Apr. 19, 2014—(GB) Search Report—App GB1322423.3.
Mar. 10, 2014—(GB) Search Report—App GB1322423.3.
May 15, 2014—(GB) Search Report—App GB1322423.3.

* cited by examiner

Figure 1 Trap in Multi-turn Coil

Figure 2  Single Turn Loop with Transformer

Figure 3  Trap in Single Turn Coil

Figure 4  Coil Following the Curved H-Field Lines

TECHNIQUES FOR CO-SITING A METAL DETECTOR WITH ANOTHER DETECTOR

CROSS REFERENCE TO RELATED APPLICATIONS

This application claims priority from UK Patent Application No. 1322423.3, filed on Dec. 18, 2013. The contents of UK Patent Application No. 1322423.3 are hereby incorporated by reference. The present application presents various applications and improvements to the system disclosed in UK Patent Application No. 1322423.3.

TECHNICAL FIELD

Various aspects relate to techniques for co-siting a metal detector with another detector, and in particular another electromagnetic (EM) or magnetic field based detector. Particular embodiments relate to techniques which allow the metal detector and the other EM or magnetic field based detector to co-inhabit each other's zones of detection, such that the two detectors may be mounted on the same detector head.

BACKGROUND

It can be advantageous to provide two different electromagnetic detectors on the same detector head. However, problems can arise with the two detectors interfering with each other. The sensing head of a metal detector usually consists of one or two coils each comprising a large number of turns of wire. A large number of turns are needed to give a high voltage output and hence high sensitivity. This represents a large mass and area of conductor that has a complex fine structure, and can make it difficult to operate other sensors on the same head.

BRIEF SUMMARY

Various embodiments described herein present several different techniques to allow a metal detector coil to be placed on the same sensing head as the sensor antenna of another detector. In a first technique one or more tuned circuits ("traps") are placed in series in the metal detector coil, tuned to the operating frequency of the other sensor. One or more of these traps can be placed around the metal detector coil to achieve isolation at several different frequencies. The effect of the traps is to make it appear as if there is a break in the coil at the selected frequency, which helps reduce the effect of the coil on the operation of the other sensor, when operated at the selected frequency.

In another technique a small number of turns, or more preferably a single turn, coil of wire is used as the metal detector coil, in combination with a step up transformer at the coil feed, to increase the EMF of the coil to desired operational levels. This reduces the mass of metal forming the metal detector coil within the sensing field of the other sensor, and is a simpler structure. Again, one or more tuned circuit traps can also be included in the circuit, tuned to the frequency of operation of the other sensor, as described above.

In a further technique, the metal detector coil is formed in a plane that has regard to the sensing field of the other sensor. More particularly, the coil is formed in a plane, typically a curved plane, which follows the magnetic field of the other sensor. In particular, the wires forming the coil are arranged in a plane that is parallel to the magnetic field lines from the other sensor so that there is no EMF induced in them. That is, the coil is formed in a plane, usually a curved plane, that is parallel to the magnetic field lines or has substantially zero net magnetic flux due to emissions from the other sensor across the plane. Such an arrangement helps to minimize any unwanted coupling or interference between the metal detector coil and the detection field of the other sensor.

In another technique, the feed for the metal detector coil comprises a twisted pair of wires, that are routed along a known axis of symmetry, usually a central axis, of the other sensor antenna, in order to try and minimize and equalize the effect of the metal detector feed on the operation of the other antenna. In addition, the metal detector feed may preferably be encased in a metal tube, to further try and isolate the feed from the other sensor antenna.

In some embodiments, several or all of the above described techniques may be used in combination. For example, the metal detector coil may comprise a single turn connected by a step-up transformer, be provided with a tuned circuit trap at the frequency of operation of the other sensor, and be positioned such that the plane of the metal detector coil follows the magnetic field of the other sensor, so that the coil is subject to substantially zero net magnetic flux through the coil.

A wide variety of other sensors might be used, but various embodiments described herein apply particularly to those using a static or time-varying magnetic field. For example, other sensors might include NQR (Nuclear Quadrapole Resonance) sensors, NMR (Nuclear Magnetic Resonance) sensors or ESR (Electron Spin Resonance) sensors.

In view of the above, one aspect provides a metal detector sensing coil, comprising one or more turns of wire; and a tuned circuit that is effectively in series with the one or more turns of wire, the tuned circuit being arranged such that its resonant frequency is a frequency of operation of another sensor antenna co-sited with the metal detector sensing coil.

In one embodiment the coil comprises a single turn of wire, the coil being connected to an antenna feed via a step up transformer. In another embodiment, the coil comprises a small number of turns, fed from an antenna feed via a step up transformer, but in this case by a transformer with a lower transformation ratio such that the same EMF is obtained as in the case with the single turn. In another embodiment the coil comprises multiple turns of wire, the multiple turns being encased along a portion of their length within a helically wound conductive sheath, the conductive sheath forming part of the tuned circuit.

In one arrangement the tuned circuit comprises a capacitor arranged in parallel with a helical winding formed from the turn or one of the turns of the sensing coil.

In one arrangement there is also provided a metal detector sensing coil comprising one or more turns of wire arranged as if on a plane that follows a magnetic field of another sensor antenna co-sited with the metal detector sensing coil. Within such an arrangement the one or more turns of wire experience substantially zero net magnetic flux from the magnetic field of the other sensor over its area.

In one arrangement there is also provided a metal detector sensing coil, wherein the coil is fed via a feed that extends along an axis, such as an axis of symmetry, and preferably the central axis of another sensor antenna co-sited with the metal detector sensing coil.

Within such an arrangement the feed may be a twisted wire pair; and/or may be encased in a metal tube along at least part of its length. In one arrangement the feed is encased in the metal tube for a majority of the portion of the feed that is within the volume of the antenna of the other sensor.

Various other features, aspects and arrangements according to embodiments will be apparent from the appended claims.

DESCRIPTION OF THE DRAWINGS

Further features and advantages will become apparent from the following description of an embodiment thereof, presented by way of example only, and by reference to the drawings, wherein like reference numerals refer to like parts, and wherein.

DETAILED DESCRIPTION

Figure 5:
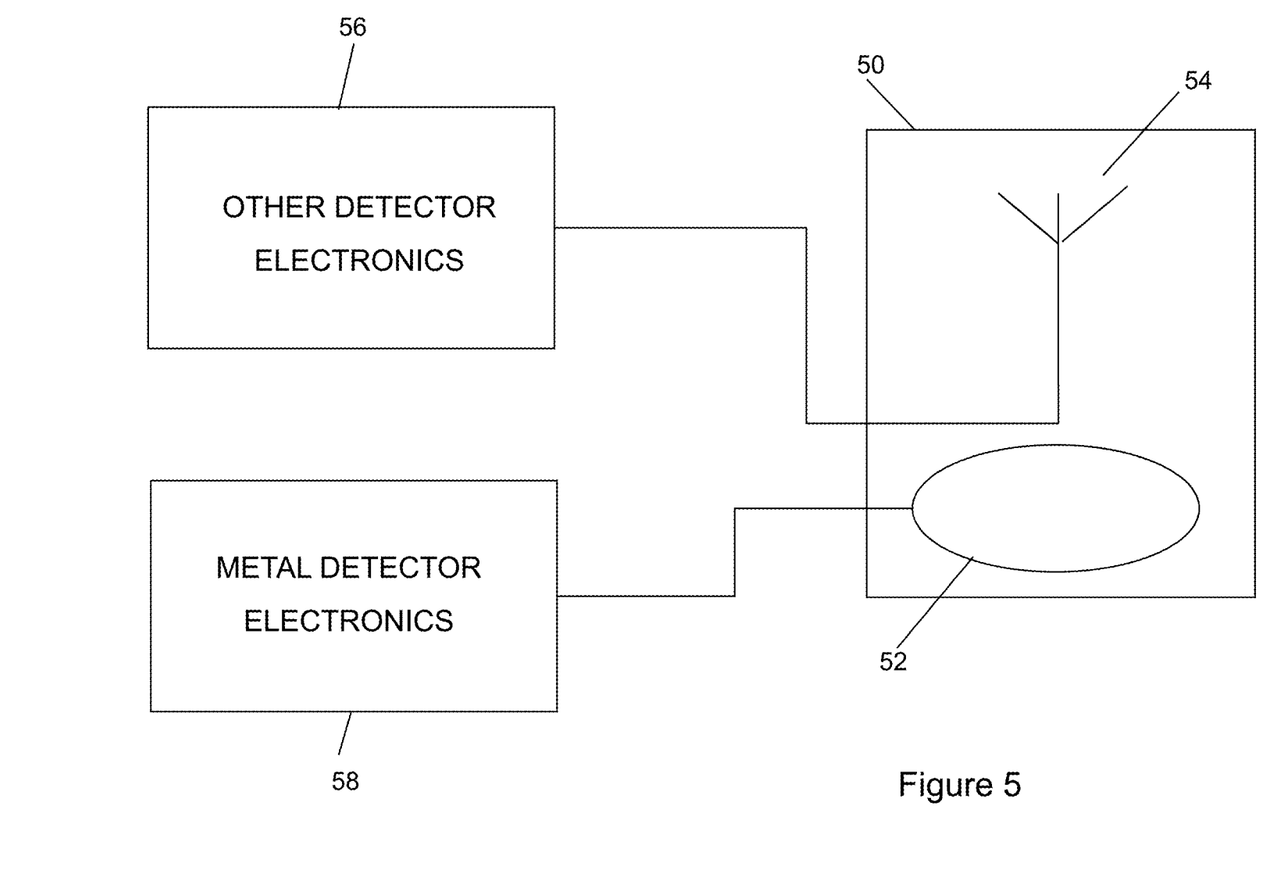
FIG. 5 is a block diagram of the general arrangement of various embodiments.

FIG. 5 illustrates the general arrangement that provides the background for various embodiments. A sensor head 50 provides a common platform for the sensing antennas 52 and 54 respectively of a metal detector and another detector, such as any of a NQR (Nuclear Quadrapole Resonance) sensor, NMR (Nuclear Magnetic Resonance) sensor, ESR (Electron Spin Resonance) sensor, or any other sensor for detecting buried objects. The respective sensing antennas 52 and 54 respectively feed their own sensor electronics packs to provide for signal detection and discrimination. Specifically, metal detector sensor coil 52 feeds metal detector electronics pack 58, whereas the antenna 54 of the other sensor feeds the other sensor electronics pack 56. The precise operation of either the metal detector electronics pack 58 or the other sensor electronics pack 56 to provide detection signals is beyond the scope of the present application, but the operation of metal detectors and other types of H field sensors is well known in the art.

In order to prevent the coil 52 of the metal detector from interfering with the operation of the other sensor, various integration techniques have been developed, providing several embodiments. These different integration techniques are described in detail next. Please note that any number of the following integration techniques, from any single such technique up to and including all of them, may be used in combination with each other in various embodiments.

Figure 1:
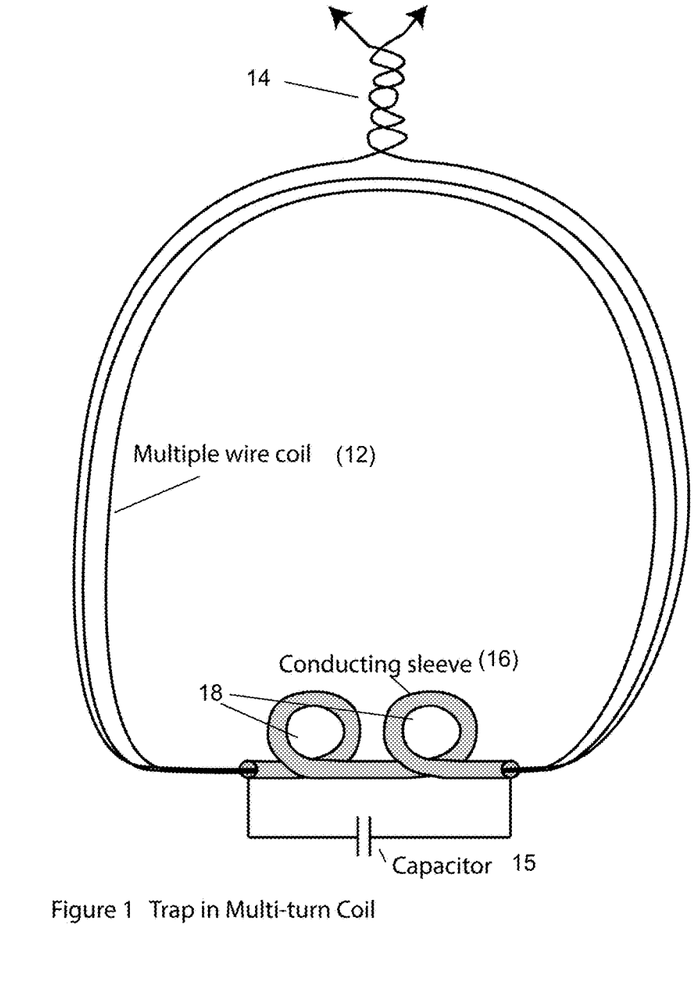
FIG. 1 is a diagram of a first embodiment.

FIG. 1 illustrates a first such integration technique, for use with metal detector coils with multiple turns. A multi-turn coil will appear as a shorted turn over a wide frequency range. This can be avoided at particular frequencies by placing a tuned circuit (trap) in the bunch of wires forming the coil. One way of achieving this is shown in FIG. 1. The wires 12 of the coil are placed in a short tubular conductive sleeve 16 for a part of their length, and this tube/bunch of wires is formed into a small helical coil 18. A capacitor 15 is then connected across the ends of the conductive sleeve 16 so as to form a tuned circuit that is tuned to the frequency at which the other sensor operates. The tubular sleeve acts as a faraday cage, and places a break in all the coil wires at the tuned frequency. The helical arrangement of the sleeve in combination with the capacitor forms an LC resonant circuit, with the capacitor value selected such that the resonant combination is resonant at the frequency of operation of the other sensor.

Alternatively, the capacitor may be connected across just one of the wires in the bunch that forms the helical coil, and the choking effect is achieved in all the wires in the bunch by virtue of their close proximity and inductive coupling to each other.

One or more of these traps may be placed around the metal detector coil to achieve isolation at several different frequencies.

Figure 2:
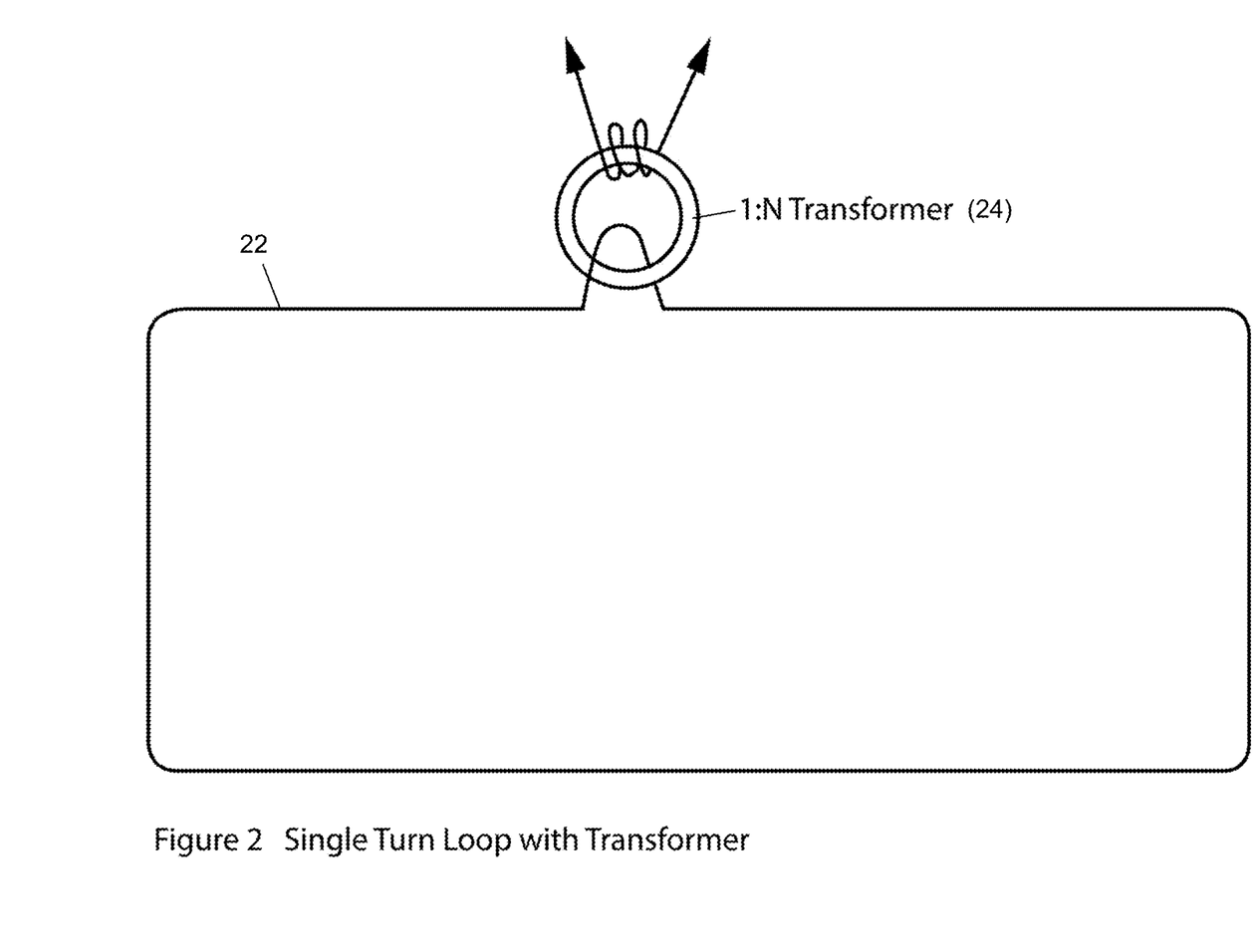
FIGS. 2 and 3 are diagrams of a second embodiment.
Figure 3:
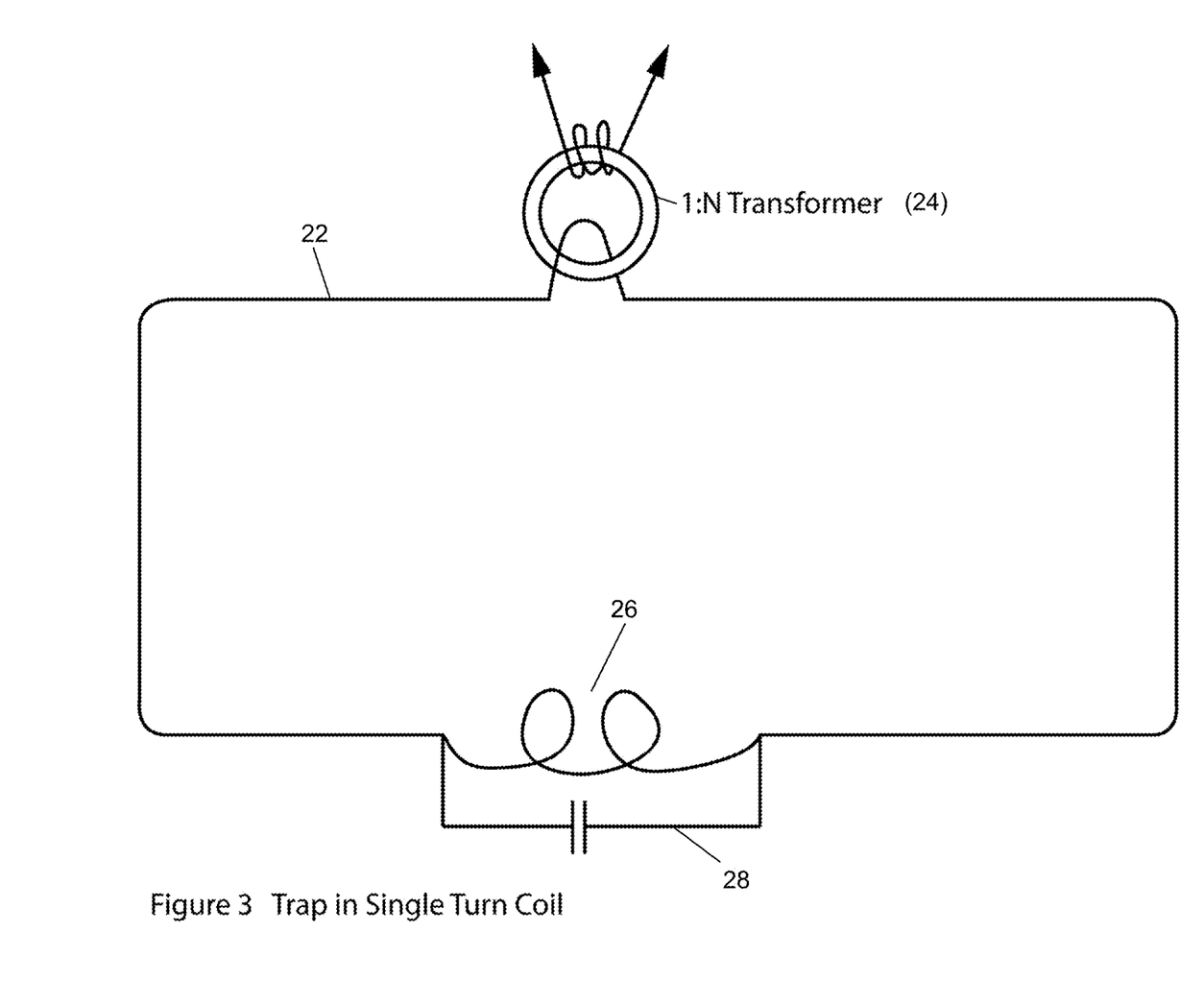

FIGS. 2 and 3 illustrate a second integration technique, which may be used on its own, or in combination with the first integration technique. In the arrangement of FIG. 1 a multi-turn coil is used in order to obtain a higher EMF than is available from a single turn. An alternative way of obtaining the high EMF is to use a single turn coil 22, but with a transformer 24 to step up the voltage to the feed, as shown in FIG. 2. Then, only a single turn of wire is needed for the coil. This will use less copper and be less obtrusive to the other sensor than a multi-turn coil. It should also be much easier to manufacture, as well as to shape into different shapes, as described in the third integration technique below.

In addition, using a single turn of wire as the metal detector coil means that it is also much easier to form such a single wire into a helical coil to make one or more traps, as shown in FIG. 3. These traps are tuned circuits comprising a helical coil 26 formed out of the single wire turn of the metal detector coil, connected in parallel with a capacitor 28. The resonant circuit formed by the inductor-capacitor combination is tuned to resonate at the operating frequency of the other sensor, to thereby simulate a break in the wire forming the metal detector coil at the operating frequency of the other sensor.

A variant of the second integration technique is to use multiple turns of wire in combination with a transformer 24. In this case, to achieve the same desired EMF a lower transformer transformation ratio would be required due to the multiple turns of wire, but also because of the use of the transformer fewer turns of wire are required to achieve the same EMF than the case where no transformer is used. There is in effect a reciprocal trade-off between the number of turns of wire in the metal detector sensing coil and the step up/down (transformation) ratio of the transformer, to achieve the same desired EMF, for example doubling the number of turns of wire in the sensing coil will halve the transformer step up ratio required, etc. Using fewer turns of wire gives the same advantages given above in relation to the provision of a single turn of wire, although to a lesser extent than in the case of a single turn. That is, using fewer turns of wire in combination with a transformer means that less copper is used than the case with no transformer and a higher number of turns, which makes the coil less obtrusive to the other sensor, and easier to form into desired shapes, as described below. Effectively, the variant provides a compromise position between the higher number of turns but no transformer embodiment of FIG. 1, and the single turn, transformer with higher step-up/down ratio embodiment of FIG. 2. In practice a small number of turns would preferably be used, for example between 50 and 100 turns, 50 or fewer turns, 30 or fewer turns, 10 or fewer turns, 5 or fewer turns, or even any of 4, 3, or 2 turns.

Figure 4:
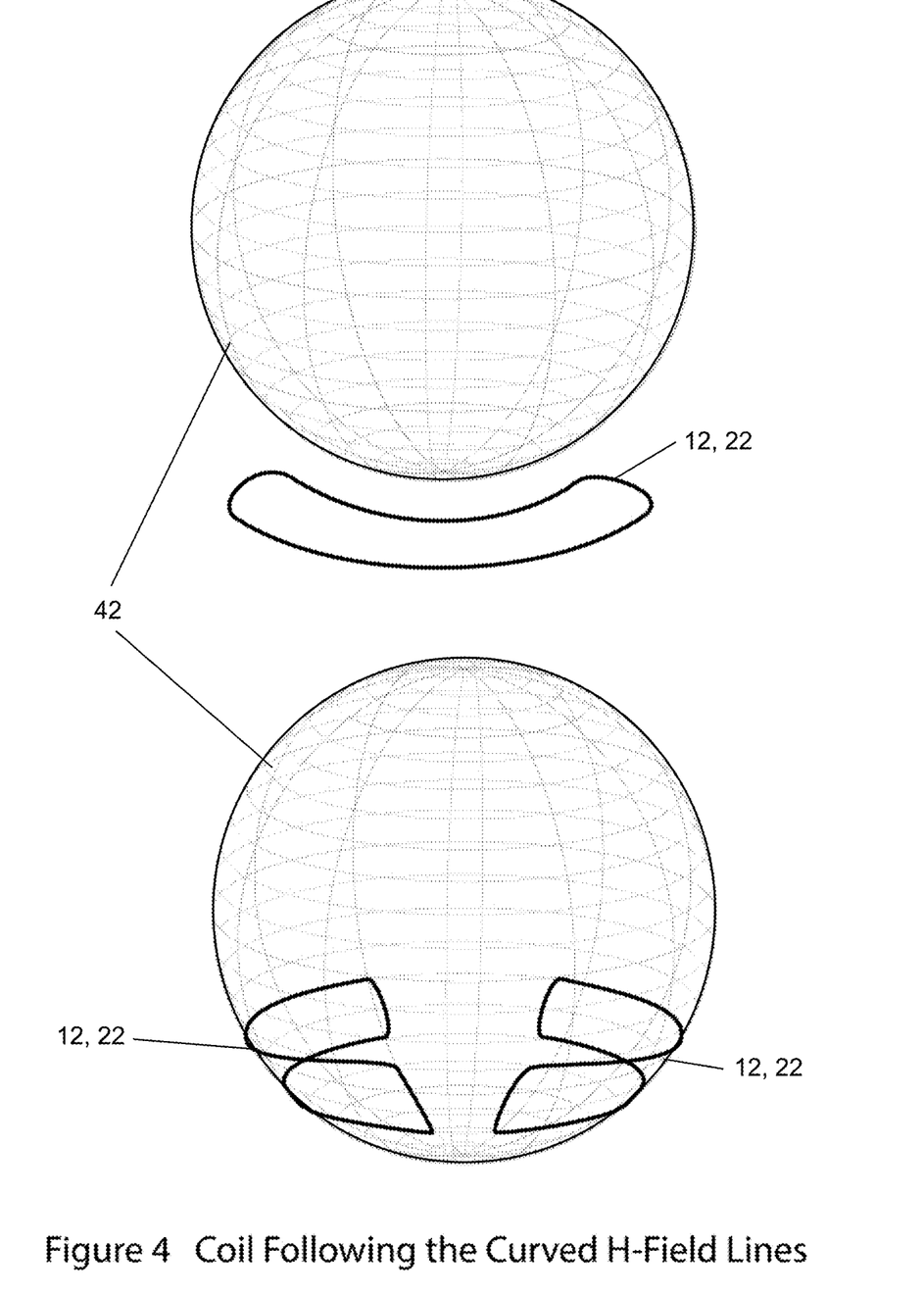
FIG. 4 is a diagram of arrangements according to a third embodiment.

FIG. 4 illustrates a third integration technique, concerned with the physical placement of the metal detector coil with respect to the magnetic field of the other sensor. The ideal position for a metal detector coil from a theoretical viewpoint would be with its plane perpendicular to any other sensor coils, and centered symmetrically on them, for example in an equatorial plane, so that the coil wire was parallel to the H fields from those coils and did not couple to them. However, such an ideal position places it further from the ground, and decreases the effective detection range, so the next best solution is to mount it or them symmetrically beneath the other sensor, as shown in FIG. 4.

In particular, as shown in FIG. 4, the metal detector coils 12, 22 are wound as if on a curved surface, such that their planes are parallel to the magnetic field lines 42 from the other sensor and they have no net magnetic flux through them. Such an arrangement will minimize the magnetic coupling to the other sensor.

As shown in FIG. 4 (upper), this is achieved by first shaping the coil in a curved configuration, to match the curves of the magnetic field lines of the other sensor. The curved configuration is then projected on to the three dimensional arrangement of the field lines as shown in FIG. 4 (lower). FIG. 4 (lower) shows that at least two metal detector coils may be mapped onto the field lines of the other sensor, arranged symmetrically.

Practically, in order to produce the above, the metal detector coil may be formed as a printed circuit board (PCB) trace on a suitably shaped dielectric support board.

Figure 6:
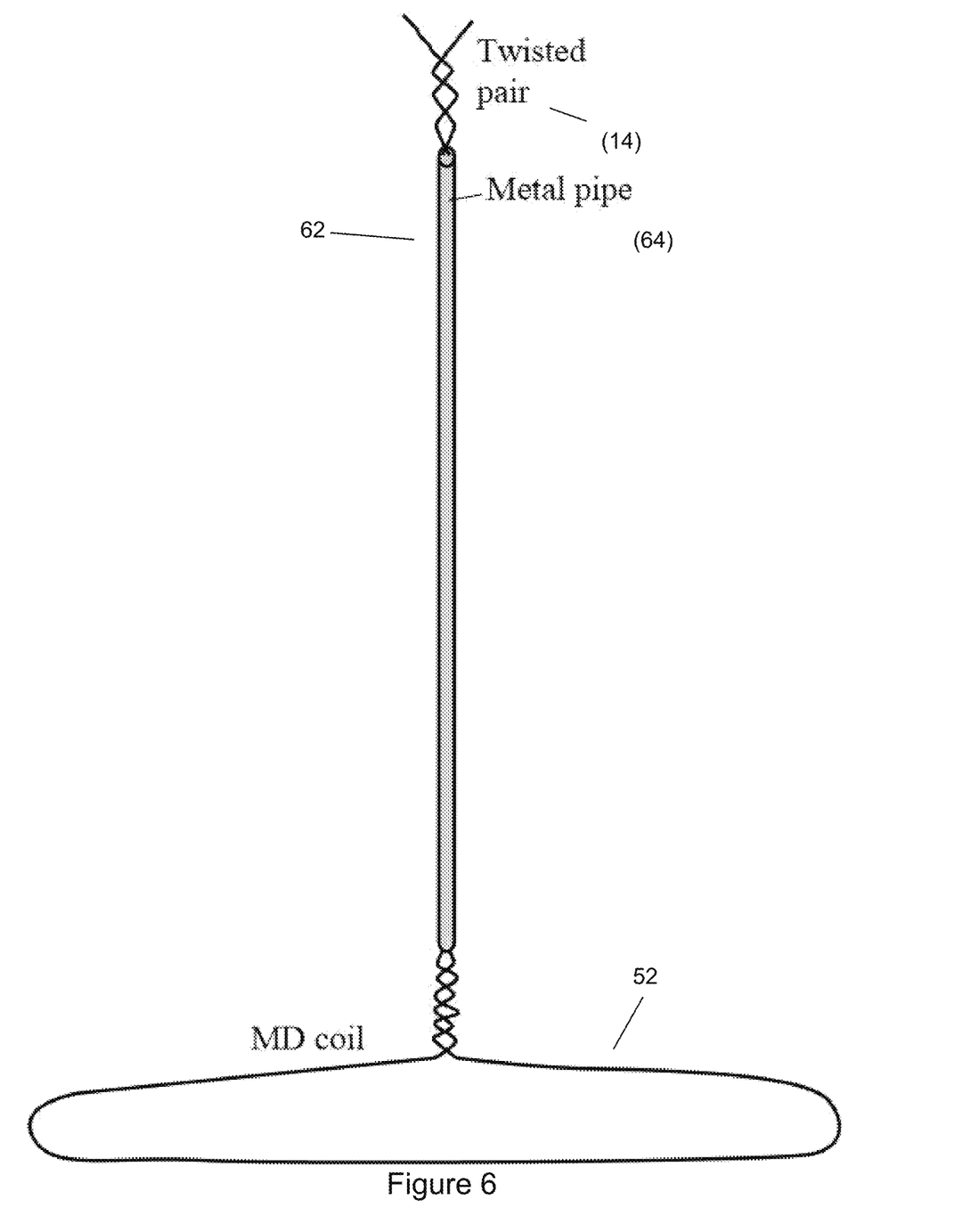
FIG. 6 is a diagram of the fourth embodiment.

A further, fourth, integration technique is shown in FIG. 6. The metal detector loop 52 is fed via a twisted wire pair feed 14 that extends along an axis, such as an axis of symmetry, and preferably the central axis, of the antenna of the other sensor. The twisted wire pair feed is in this embodiment encased in a metal tube along its length where it extends within the other sensor. This metal tube helps to isolate the feed from the other sensor, and vice versa. With such a feed arrangement the effect of the feed arrangements of the two sensors (i.e. the metal detector loop 52 and the other sensor) on their sensing ability is minimized, or can be easily compensated for by the signal processing performed in the respective detector electronics packs 56 and 58.

It will be appreciated that the above described integration techniques may be applied in any combination. For example, the first and the second techniques may be used together, or the first and the third techniques. In addition, the second and the third techniques may also be used together. Likewise, the fourth technique may be used in combination with any or all of the first three described techniques, particularly where the other antenna is of a suitable shape. In some embodiments, all four techniques may be used together in combination.

There follows a series of numbered features defining particular embodiments. Where a numbered feature refers to one or more earlier numbered features then those features may be considered together in combination.

1. A metal detector sensing coil feature, comprising:
    one or more turns of wire; and
    a tuned circuit which is effectively in series within the one or more turns of wire, the tuned circuit being arranged such that its resonant frequency is a frequency of operation of another sensor antenna co-sited with the metal detector sensing coil.

2. A metal detector sensing coil according to feature 1, wherein the coil comprises a single turn of wire or a small number of turns of wire, preferably 100 turns or fewer, the coil being fed from an antenna feed via a transformer having a transformation ratio selected in dependence on the number of turns of wire in the coil such that the coil provides a desired EMF.

3. A metal detector sensing coil according to features 1 or 2, wherein the coil comprises multiple turns of wire, the multiple turns being encased along a portion of their length within a helically wound conductive sheath, the conductive sheath forming part of the tuned circuit.

4. A metal detector sensing coil according to any of the preceding features wherein the tuned circuit comprises a capacitor arranged in parallel with a helical winding formed from the turn or one of the turns of the sensing coil, or from a conducting sheath arranged over said coil.

5. A metal detector sensing coil according to any of the preceding features, wherein the one or more turns of wire experience substantially zero net magnetic flux from the magnetic field of the other sensor.

6. A metal detector sensing coil according to feature 5, wherein the one or more turns of wire are arranged as if on a plane that follows the magnetic field lines of the other sensor, and/or is/are substantially parallel to the flux lines at each position along the or each turn.

7. A metal detector sensing coil according to feature 5, wherein the substantially zero net flux is achieved by having a substantially equal amount of magnetic flux from the magnetic field of the other sensor passing through the sensing coil in opposite directions so as to cancel out.

8. A metal detector according to feature 5, wherein:
    i) the one or more turns of wire are arranged as if on a plane that follows the magnetic field lines of the other sensor, and/or is/are substantially parallel to the flux lines at each position along the or each turn; and
    ii) a substantially equal amount of magnetic flux from the magnetic field of the other sensor passes through the sensing coil in opposite directions so as to cancel out; whereby to provide for substantially zero net magnetic flux.

9. A metal detector sensing coil according to any of the preceding features, wherein the coil is fed via a feed that extends along an axis, such as an axis of symmetry, and preferably a central axis, of the antenna of the other sensor.

10. A metal detector sensing coil according to feature 9, wherein the feed is a twisted wire pair.

11. A metal detector sensing coil according to features 9 or 10, wherein the feed is encased in a metal tube along at least part of its length.

12. A metal detector sensing coil according to feature 11, wherein the feed is encased in the metal tube for a majority of the portion of the feed that is within the volume of the antenna of the other sensor.

13. A metal detector sensing coil feature, wherein the coil comprises a single turn of wire or a small number of turns of wire, preferably 100 or fewer, fed from an antenna feed via a transformer having a transformation ratio selected in dependence on the number of turns of wire in the coil such that the coil provides a desired EMF.

14. A metal detector sensing coil according to feature 13, wherein the turn or turns of wire experience substantially zero net magnetic flux from the magnetic field of the other sensor.

15. A metal detector sensing coil according to feature 14, wherein the turn or turns of wire is/are arranged as if on a plane that follows the magnetic field lines of the other sensor, and/or is/are substantially parallel to the flux lines at each position along the turn.

16. A metal detector sensing coil according to feature 14, wherein the substantially zero net flux is achieved by having a substantially equal amount of magnetic flux from the magnetic field of the other sensor passing through the sensing coil in opposite directions so as to cancel out.

17. A metal detector according to feature 14, wherein:
  i) the turn or turns of wire is/are arranged as if on a plane that follows the magnetic field lines of the other sensor, and/or is/are substantially parallel to the flux lines at each position along the turn; and
  ii) a substantially equal amount of magnetic flux from the magnetic field of the other sensor passes through the sensing coil in opposite directions so as to cancel out; whereby to provide for substantially zero net magnetic flux.
18. A metal detector sensing coil according to any of features 13 to 17, wherein the coil is fed via a feed that extends along an axis, such as an axis of symmetry, and preferably a central axis, of the antenna of the other sensor.
19. A metal detector sensing coil according to feature 18, wherein the feed is a twisted wire pair.
20. A metal detector sensing coil according to features 18 or 19, wherein the feed is encased in a metal tube along at least part of its length.
21. A metal detector sensing coil according to feature 20, wherein the feed is encased in the metal tube for a majority of the portion of the feed that is within the volume of the antenna of the other sensor.
22. A metal detector sensing coil feature comprising one or more turns of wire, arranged such that the one or more turns of wire experience substantially zero net magnetic flux from the magnetic field of another sensor antenna co-sited with the metal detector sensing coil.
23. A metal detector sensing coil according to feature 22, wherein the one or more turns of wire are arranged as if on a plane that follows the magnetic field lines of the other sensor, and/or is/are substantially parallel to the flux lines at each position along the or each turn.
24. A metal detector sensing coil according to feature 22, wherein the substantially zero net flux is achieved by having a substantially equal amount of magnetic flux from the magnetic field of the other sensor passing through the sensing coil in opposite directions so as to cancel out.
25. A metal detector sensing coil according to feature 22, wherein:
  i) the one or more turns of wire are arranged as if on a plane that follows the magnetic field lines of the other sensor, and/or is/are substantially parallel to the flux lines at each position along the or each turn; and
  ii) a substantially equal amount of magnetic flux from the magnetic field of the other sensor passes through the sensing coil in opposite directions so as to cancel out;
  whereby to provide for substantially zero net magnetic flux.
26. A metal detector sensing coil according to any of features 22 to 25, wherein the coil is fed via a feed that extends along an axis, such as an axis of symmetry, and preferably a central axis, of the antenna of the other sensor.
27. A metal detector sensing coil according to feature 26, wherein the feed is a twisted wire pair.
28. A metal detector sensing coil according to features 26 or 27, wherein the feed is encased in a metal tube along at least part of its length.
29. A metal detector sensing coil according to feature 28, wherein the feed is encased in the metal tube for a majority of the portion of the feed that is within the volume of the antenna of the other sensor.
30. A metal detector sensing coil feature, wherein the coil is fed via a feed that extends along an axis, such as an axis of symmetry, and preferably a central axis, of another sensor antenna co-sited with the metal detector sensing coil.
31. A metal detector sensing coil according to feature 30, wherein the feed is a twisted wire pair.
32. A metal detector sensing coil according to features 30 or 31, wherein the feed is encased in a metal tube along at least part of its length.
33. A metal detector sensing coil according to feature 32, wherein the feed is encased in the metal tube for a majority of the portion of the feed that is within the volume of the antenna of the other sensor.
34. An object detector system feature, comprising:
  a metal detector sensing coil according to any of the preceding features; and
  another sensor antenna co-sited with the metal detector sensing coil;
  wherein the metal detector sensing coil and the other sensor antenna are so located with respect to each other as to co-inhabit each other's zones of detection.
35. A system according to feature 34, and further comprising:
  i) metal detector discriminating electronics arranged to receive signals from the metal detector sensing coil and discriminate object detection related signals therein; and
  ii) other sensor discriminating electronics arranged to receive signals from the other sensor antenna and discriminate object detection related signals therein.

Various modifications to the above described embodiments, whether by way of addition, deletion or substitution, will be apparent to the skilled person to provide additional embodiments, any and all of which are intended to be encompassed by the appended claims.

The invention claimed is:
1. A metal detector sensing coil, comprising:
  multiple turns of wire overlapping each other; and
  a tuned circuit in series with the multiple turns of wire, the tuned circuit being arranged such that its resonant frequency is a frequency of operation of another sensor antenna co-sited with the metal detector sensing coil,
  wherein the tuned circuit comprises:
    a helically wound tubular conductive sheath encasing a portion of a length of the multiple turns of wire;
    wherein a portion of each turn of the multiple turns of wire is encased in a single turn of the helically wound tubular conductive sheath; and
    a capacitor connected in parallel with the tubular conductive sheath.
2. The metal detector sensing coil according to claim 1, wherein the multiple turns of the wire experience substantially zero net magnetic flux from a magnetic field of the another sensor antenna.
3. The metal detector sensing coil according to claim 1, wherein the coil is fed via a feed that extends along an axis of the another sensor antenna.
4. An object detector system, comprising:
  the metal detector sensing coil according to claim 1; and
  the other sensor antenna co-sited with the metal detector sensing coil;
  wherein the metal detector sensing coil and the other sensor antenna are located with respect to each other as to co-inhabit each other's zones of detection.
5. The object detector system according to claim 4, and further comprising:
  i) metal detector discriminating electronics arranged to receive signals from the metal detector sensing coil and discriminate object detection related signals therein; and
  ii) other sensor discriminating electronics arranged to receive signals from the other sensor antenna and discriminate object detection related signals therein.

6. The metal detector sensing coil according to claim 1, further comprising one or more additional tuned circuits arranged over different portions of the length of the one or more turns of wire and arranged having different resonant frequencies.

7. A metal detector sensing coil comprising:

one or more turns of wire; and a tuned circuit in series with the one or more turns of wire, the tuned circuit being arranged such that its resonant frequency is a frequency of operation of another sensor antenna co-sited with the metal detector sensing coil, wherein the tuned circuit comprises:

a helically wound tubular conductive sheath encasing a portion of a length of the one or more turns of wire; wherein a portion of each turn of the one or more turns of wire is encased in a single turn of the helically wound tubular conductive sheath; and a capacitor connected in parallel with the tubular conductive sheath;

wherein the metal detector sensing coil further comprises one or more additional tuned circuits arranged over different portions of the length of the one or more turns of wire and arranged having different resonant frequencies.

8. A metal detector sensing coil comprising:

multiple turns of wire overlapping each other, arranged such that the multiple turns of wire experience substantially zero net magnetic flux from a magnetic field of another sensor antenna co-sited with the metal detector sensing coil;

a helically wound tubular conductive sheath encasing a portion of a length of the multiple turns of wire; wherein a portion of each turn of the multiple turns of wire is encased in a single turn of the helically wound tubular conductive sheath; and a capacitor connected in parallel with the tubular conductive sheath so as to form a circuit tuned to a frequency of operation of the other sensor antenna.

9. The metal detector sensing coil according to claim 8, wherein the multiple turns of wire are arranged substantially on a curve formed along magnetic field lines of the other sensor, and wherein the multiple turns of wire are substantially parallel to flux lines of the other sensor.

10. An object detector system, comprising:

the metal detector sensing coil according to claim 8; and the other sensor antenna co-sited with the metal detector sensing coil;

wherein the metal detector sensing coil and the other sensor antenna are so located with respect to each other as to co-inhabit each other's zones of detection.

\* \* \* \* \*